United States Patent

Bot et al.

[11] Patent Number: 5,807,844
[45] Date of Patent: Sep. 15, 1998

[54] PRODUCTION OF TOXIN BINDING BIOPOLYMERS, USE THEREOF

[76] Inventors: György Bot, Bemtér 18/b, H-4026 Debrecen; Sándor Sipka, Kürigyarpiat u. 64, H-4032 Debrecen; Pál Gergeley, Komlóssv u. 64, H-4032 Debrecen; Gyula Szegedi, Illvos u. 18, H-4032 Debrecen; Béla Toth, Dóczy J. u. 26, H-4032 Debrecen; Ilona Farkas, Szappanos u. 16/a, H-4029 Debrecen; Katalin Várnai, Diosarok U. 16/III, H-1125 Budapest, all of Hungary

[21] Appl. No.: 537,922
[22] PCT Filed: May 6, 1994
[86] PCT No.: PCT/HU94/00011
§ 371 Date: Nov. 1, 1995
§ 102(e) Date: Nov. 1, 1995
[87] PCT Pub. No.: WO94/26921
PCT Pub. Date: Nov. 24, 1994

[30] Foreign Application Priority Data

May 11, 1993 [HU] Hungary .............. P 93 01368

[51] Int. Cl.$^6$ .............. A61K 31/715; A61K 38/43; C12P 19/18; C08B 31/00
[52] U.S. Cl. .............. 514/58; 514/54; 514/59; 514/60; 435/97; 435/101; 435/102; 435/103; 536/102; 536/103; 536/112; 536/126; 424/94.4; 424/94.61
[58] Field of Search .............. 435/97, 101, 102, 435/103; 514/54, 58, 59, 60; 536/102, 103, 112, 126; 424/94.4, 94.61

[56] References Cited

U.S. PATENT DOCUMENTS

| | | | |
|---|---|---|---|
| 58,371 | 10/1866 | Boyes | 424/646 |
| 2,076,889 | 4/1937 | Hees | 514/60 |
| 3,852,475 | 12/1974 | Tarangul | 424/361 |
| 3,980,772 | 9/1976 | Ginger et al. | 424/94 |
| 4,120,952 | 10/1978 | Cardon | 424/180 |
| 5,112,864 | 5/1992 | Djuric et al. | 514/549 |
| 5,460,961 | 10/1995 | Deby et al. | 435/192 |
| 5,545,721 | 8/1996 | Carroll et al. | 530/391.7 |

OTHER PUBLICATIONS

Cori et al, J. Biol. Chem. 15/:39–55, 1943.
Goldemberg, Biochim. Biophys. Acta 56:357–359, 1962.
Smith, Arch. Biochem. Biophys. 146:380–390, 1971.
Hassid et al, J. Biol. Chem. 148:89–96, 1943.
Merck Index, 11$^{th}$ Ed., Budavari et al, eds., pp. 464, 465, 1386 (1989).

*Primary Examiner*—Francisco C. Prats
*Attorney, Agent, or Firm*—Beveridge, DeGrandi, Weilacher & Young, LLP

[57] ABSTRACT

A method for production of toxin-binding, non-toxic, modified, biopolymers and the use thereof for the treatment of septic shock, infections and toxic states and to the use of them as carriers for transportation of biologically or therapeutically important materials (enzymes or drugs) into phagocytes or cells bearing Fc and complement receptors and as a natural source of energy for cells. The toxin binding, non-toxic structurally modified biopolymers are prepared by the reaction of polysaccharides containing alpha 1,4 or 1,6 linkages with glucose-1-phosphate catalyzed by glycogen phosphorylase enzyme in a buffer solution at pH 6.8–7.4 at a temperature of 20°–30° C. and by the separation of the obtained biopolymers in a well-known manner.

4 Claims, No Drawings

PRODUCTION OF TOXIN BINDING BIOPOLYMERS, USE THEREOF

This invention relates to a method for production of toxin-binding, non-toxic, modified carbohydrate biopolymers.

The invention also relates to the use thereof for the treatment of septic shock, infections and toxic states, and to the use of them as carriers for transportation of biologically or therapeutically important materials (enzymes or drugs) into phagocytes or cells bearing Fc and complement receptors.

Adsorption of various toxic agents by materials of large surface as kaolin, aluminium or/and magnesium silicates (GUT 34, 51–55, 1993) can result in a detoxification effect. The disadvantage of these adsorbents is their intolerability for human organism.

Non-toxic adsorbents metabolised in the cells or in the organism—termed in the present description as toxin binding non-toxic biopolymers (TBNTBP)—can solve this contradiction.

We have found that non-toxic, structurally modified biopolymers can be prepared by synthetic way and these biopolymers are similar to the native polymers which are metabolized in the organism by physiological pathways.

According to this invention the non-toxic biopolymers may be produced from polysaccharides containing alpha-1,4 or 1,6 linkages. According to the inventive process the polysaccharides containing alpha-1,4 or 1,6 linkages are reacted with D-glucose-1-phosphate in the presence of glycogen phosphorilase enzyme, in buffer solution at pH 6,8–7,4 at the temperature of 20°–30° C. and the obtained biopolymers are separated by well-known methods. Polysaccharides (containing 1,4 or 1,6 linkages) advantageously glycogen, amylopectin, dextrin or the mixtures thereof can serve as acceptor molecules, "primers" for the chain-elongation process.

Besides glycogen, amylopectin, and dextrin other polymers of homo- and heteroglycans can also be used as "primer" polysaccharides. In general, all types of glycan molecules containing glucose units with alpha-1,4 or 1,6 bond types can serve as templates for the reactions.

The inventive process for the production of biopolymers is an enzymatic elongation of the respective chains in the soluble polysaccharides (glycogen and other glycans with alpha-1,4 or 1,6 linkages or the mixture of them ) by the enzyme glycogen phosphorylase 'a' or 'b' (EC 2.4.1.1) and the substrate D-glucose-1-phosphate resulting in a insoluble, "coarse disperse", colloidal particles with average size (diameter) not larger than 1 micrometer.

Both phosphorilase 'a' and 'b' can be used as catalysts for the side-chain elongation reactions (the addition of adenosine-5'-monophosphate [AMP] is also required when phosphorilase 'b' is used).

The biopolymers can be produced in the presence of phosphorilase with specific activity of 50–55 IU/mg in pH 6.8–7.4 buffer solution (for example Tris-HCl or sodium beta-glycerophosphate completed with EDTA, beta-mercaptoethanol or NaF etc.) at 25°–30° C. during 20–30 min incubation time.

After precipitation of polymer with trichloro acetic acid (TCA) and resuspension of pellet in buffer, the precipitation of final biopolymer particles is taking place on the influence of cold ethanol treatment.

Advantageously we react 1 part of weight of polysaccharide containing 1,4 or 1,6 linkages with 0,5–1,5 part of weights of D-glucose-1-phosphate in the presence of 50–200 IU of phosphorylase enzyme.

If we use a mixture of glycogen with other polysaccharides as starting material, the rate of weight of the components is between 0,2:1–2:1.

According to this invention we have found that structurally modified biopolymers with alpha-1,4 or 1,6 linkages can be used ill septic shock, infections, acute phase reactions, and toxic states it is common that a great number of pathologic substances and mediator agents as cytokines, enzymes, lipid mediators, biogen amines, acute phase proteins, toxins are simultaneously present in the collapsed circulation, representing the state of multiple organ dysfunction syndrome. In the therapy of such cases the use of one or two antidotes can not be enough. The toxin binding biopolymers, like the structurally modified derivatives of glycogen, however, can bind simultaneously numerous toxic or pathologic molecules. They can transport these substances into the lysosomes of phagocytes where the biochemical degradation of both the pathologic and the adsorbent, carrier molecules can take place. It is a special advantage of the glycogen derivatives that their end-product, glucose, formed by lysosome degradation, can still serve as a source of energy for the metabolically paralysed cells. Since, the adsorbents can bind also immunoglobulins and complement factors, mainly C3b, in plasma, they enter the phagocytes (or other cells) via Fc and complement, mainly CR1 receptors.

The toxin binding, non-toxic biopolymers (TBNTBP) can offer a better therapy of septic shock, severe acute infections, and any toxic states by simultaneous binding of a series of toxins or other molecules occurring in pathologic concentration in the circulation, transporting them into the lysosomes of phagocytes where the biochemical degradation of the toxins and other molecules can take place.

The structurally modified biopolymers, which are produced by this invention are not only non-toxic agents for the organism but they can selectively serve as source of energy for cells engulfing them. Among these cell types are the toxin damaged phagocytes or leukaemic, and further types of cells bearing Fc or complement receptors, able to internalize opsonized particles.

The usefulness of TBNTBP can summarized as:
(a) enlarged adsorbent capacity compared to soluble glycogen or other polysaccharides,
(b) carrier function for toxic, pathologic molecules resulting in a detoxificating effect,
(c) carrier function for biologically or therapeutically important molecules (enzymes or drugs) in order to restore the normal functions of the cells.

The following examples illustrate the process for the production of TBNTBP and the use thereof.

EXAMPLE 1

1 g glycogen is mixed in 10 ml TEM buffer (TEM buffer: 40 mM Tris-HCl, pH 7.2, 10 mM beta-mercaptoethanol, 2 mM EDTA) with 0.73 g D-glucose-1-phosphate dissolved in 10 ml TEM and preincubated at 30° C. for 15 min. The reaction is started with the addition of 100 IU phosphorylase α in 10 ml TEM. Alter mixing the solution, incubation at 30° C. for 30 min.

Precipitation of proteins by 10 ml 10% of weight TCA and removal of precipitated protein by centrifugation (5000×g, 20° C., 10 min). The biopolymer is precipitated with the addition of 1.5 vol. of absolute ethyl alcohol and the solution is kept at 4° C. for 1 hour.

The pellet is collected by centrifugation (3000×g, 4° C., 10 min). The biopolymer with elongated side chain of glucose can be re suspended in TEM.

The suspension in TEM can be stored safely at 4° C. for one year. Prior use the pellet of biopolymer can be collected by centrifugation and resuspended in PBS (phosphate buffer in saline) physiological buffer.

Suggested concentrations of the biopolymer for in vitro use are approx. 1–2 mg/ml, for animal experiments and in vivo applications are 10–20 mg/ml.

EXAMPLE 2

The procedure is carried out according to Example 1 with the following exceptions. 150 IU of phosphorylase 'b' is used in the presence of 20 mg AMP, the pellet precipitated by absolute ethyl alcohol at 4° C. is washed and dried by acetone.

The powder can be stored at room temperature and can be suspended before use in physiological buffer, which is a mixture of 5 mM EDTA, 20 mM sodium beta-glycerophosphate, 10 mM beta-mercaptoethanol and 50 mM NaF.

EXAMPLE 3

The procedure is carried out according to Example 1 with the next exceptions. Instead of 1 g glycogen the mixture of 0.5 g glycogen and 0.5 g amylopectin is the "primer" polysaccharide.

EXAMPLE 4

The procedure is carried out according to Example 1 with the following exceptions. Instead of 1 g glycogen a mixture of 0.5 g glycogen and 0.5 g dextrin is the "primer" polysaccharide.

EXAMPLE 5

The procedure is carried out according to Example 1 with the next exceptions. Instead of 1 g glycogen a mixture of 0.66 g glycogen and 0.34 g of dextrin (with molecular mass of about 500,000) is the "primer" polysaccharide.

EXAMPLE 6

In artificial acute pancreatitis induced in dogs by injection of olive oil into the ducts Wirsungianus, the i.v. application of TBNTBP according to Example 3 (in a daily dose of 10 mg/ body weight kg for three days) could decrease the elevation of levels of lipase and amylase in plasma, and resulted in the prevention of necrosis in the pancreas.

EXAMPLE 7

In vitro addition of TBNTBP according to Example 4 alone to the monocytes of patients suffering from impaired monocyte function included a defective production of oxygen free radicals and loss of intracellular myeloperoxidase resulted in an improvement in the production of super oxide anion in these cells. When human myeloperoxidase was adsorbed to TBNTBP and added to the damaged monocytes the production of free radicals was completely restored compared to the healthy controls. TBNTBP may have double function in the series of experiments. It could serve as a source of energy and by transporting myeloperoxidase it could restore the normal functions of the cells.

EXAMPLE 8

Rat Model of Endotoxin Shock

Wistar male rats (200 g) were presensitized for endotoxin by i.v. injection of 5 mg, endotoxin free Pb-acetate. $Ld_{50}$ of i.v. E. coli lipopolysaccharid (LPS) was found 2 µg. 21 mg/kg of i.v. TBNTBP according Example 1 was applied just before LPS.

Evaluation of lethality: after 12 hours.

The experiments were carried out on five groups of rats (One group consisted of 12 animals).

The results of these experiments are illustrated in the Table 1.

TABLE 1

Protecting effect of TBNTBP according Example 1 on the endotoxin shock in rats

| Experiments on rats | Lethality, Percent of animals |
|---|---|
| 1. Pb acetate + TBNTBP | 0 |
| 2. Pb acetate + LPS ($LD_{50}$) | 50 |
| 3. Pb acetate + LPS ($LD_{50}$) + TBNTBP | 0 |
| 4. Pb acetate + LPS ($LD_{100}$) | 100 |
| 5. Pb acetate + LPS ($LD_{100}$) + TBNTBP | 40 |

EXAMPLE 9

Binding Assays

On the basis of in vitro experiments radioactive labelled E. coli LPS, human tumour necrosis factor alpha and human phospholipase $A_2$ were found to be bound dose dependently to TBNTBP according to Example 1.

E. coli LPS (lipopolysaccharide) and human PLA (phospholipase $A_2$) (14 kD) were made and purified in Debrecen in Hungary.

$^{99m}$Tc labelling of E. coli, $^{125}$I labelling of human $PLA_2$ and TNF-alpha (tumornecrosis factor alpha) was prepared in Debrecen in Hungary.

The above written compounds were solved or suspended in PBS (phosphate buffer in saline). The radioactivity was detected by a gamma counter (produced by Gamma Ltd., Hungary).

The results of the experiments are illustrated in the Table 2, Table 3, Table 4.

TABLE 2

Binding of $^{99m}$Tc E. coli lipopolysaccharide by TBNTBP acc. to Example 1

| Solution | 1 | 2 | 3 | 4 |
|---|---|---|---|---|
| TBNTBP ml | 0,25 | 0,25 | 0,25 | 0,25 |
| $^{99}$Tc LPS ml | — | 0,20 | 0,40 | 0,80 |
| PBS ml | 1,0 | 0,80 | 0,60 | 0,20 |
| 37° C. 60 min centrifugation | | | | |
| Pellet cpm | 33 | 45100 (23%) | 126653 (36%) | 285177 (44%) |
| Supernatant cpm | 45 | 149678 (77%) | 224151 (64%) | 352028 (56%) |

TABLE 3

Binding of human phospholipase $A_2$ by TBNTBP according to Example 1

| Solution | 1 | 2 | 3 | 4 |
|---|---|---|---|---|
| TBNTBP ml | 0,25 | 0,25 | 0,25 | 0,25 |
| $^{125}IPLA_2$ ml | — | 0,05 | 0,10 | 0,20 |
| PBS ml | 0,25 | 0,20 | 0,15 | 0,05 |
| 37° C. 60 min centrifugation | | | | |
| Pellet cpm | 55 | 1854 (35%) | 3392 (36%) | 6441 (38%) |

TABLE 3-continued

Binding of human phospholipase A₂ by TBNTBP according to Example 1

| Solution | 1 | 2 | 3 | 4 |
|---|---|---|---|---|
| Supernatant cpm | 40 | 3322 (65%) | 5924 (64%) | 10652 (62%) |

TABLE 4

Binding of human $^{125}$I tumour necrosis factor alpha by TBNTBP according to Example 1

| Solution | 1 | 2 | 3 | 4 |
|---|---|---|---|---|
| TBNTBP ml | 0,25 | 0,25 | 0,25 | 0,25 |
| $^{125}$ITNF-alpha ml | — | 0,025 | 0,05 | 0,10 |
| PBS ml | 0,25 | 0,225 | 0,20 | 0,15 |
| 37° C. 60 min centrifugation | | | | |
| Pellet cpm | 47 | 10703 (22%) | 27277 (26%) | 53018 (25%) |
| Supernatant cpm | 52 | 38257 (78%) | 79329 (74%) | 159626 (75%) |

EXAMPLE 10

Measurement of Platelet Aggregation

TBNTBP according to Example 1 used in vitro could block the aggregation of human platelets in platelet-rich plasma by rapid and efficient binding of aggregating agents, like adenosine-diphosphate and platelet activating factor.